United States Patent [19]

Barnett et al.

[11] Patent Number: 5,426,187
[45] Date of Patent: Jun. 20, 1995

[54] PROCESS FOR THE PREPARATION OF 4-HYDROXY-5-SUBSTITUTED ETHYNYLPYRROLO [2,3-D]PYRIMIDINE INTERMEDIATES

[75] Inventors: Charles J. Barnett, Indianapolis; Michael E. Kobierski, Greenwood, both of Ind.

[73] Assignee: Eli Lilly and Company, Indianapolis, Ind.

[21] Appl. No.: 160,010

[22] Filed: Nov. 30, 1993

[51] Int. Cl.$^6$ .................. C07D 487/04; C07F 7/18
[52] U.S. Cl. ............................ 544/280; 544/229
[58] Field of Search ........................... 544/280

[56] References Cited

U.S. PATENT DOCUMENTS

| | | | |
|---|---|---|---|
| 4,818,819 | 4/1989 | Taylor et al. | 544/279 |
| 4,996,206 | 2/1991 | Taylor et al. | 514/258 |
| 4,997,838 | 3/1991 | Akimoto et al. | 214/258 |
| 5,028,608 | 7/1991 | Taylor et al. | 514/258 |
| 5,106,974 | 4/1992 | Akimoto et al. | 544/280 |
| 5,235,053 | 8/1993 | Barnett et al. | 544/280 |
| 5,248,775 | 9/1993 | Taylor et al. | 544/280 |

OTHER PUBLICATIONS

Chauhan J.A.C.S 107, 1028 (1985).

*Primary Examiner*—Mark L. Berch
*Attorney, Agent, or Firm*—Robert A. Conrad; Steven A. Fontana; David E. Boone

[57] ABSTRACT

Processes for preparing 4-hydroxy-5-ethynylpyrrolo[2,3-d]pyrimidine intermediates and N-[4-(2-{4-hydroxypyrrolo[2,3-d]pyrimidin-3-yl}ethyl)benzoyl]-L-glutamic acid derivatives having antineoplastic activity are provided.

27 Claims, No Drawings

PROCESS FOR THE PREPARATION OF 4-HYDROXY-5-SUBSTITUTED ETHYNYLPYRROLO [2,3-D]PYRIMIDINE INTERMEDIATES

FIELD OF THE INVENTION

This invention relates to the fields of pharmaceutical and organic chemistry, and provides processes for the preparation of 4-hydroxy-5-substituted-ethynylpyrrolo[2,3-d]pyrimidines which are useful, inter alia, as intermediates in the preparation of a series of complex antifolate-type antimetabolites. The invention further relates to processes for preparing 4-hydroxypyrrolo[2,3-d]pyrimidin-L-glutamic acid derivatives which are useful as antifolate-type antimetabolites.

BACKGROUND OF THE INVENTION

Antimetabolites have been used for a number of years as chemotherapeutic agents in the treatment of cancer. One such drug, methotrexate, is now one of the most widely used anticancer drugs; and many other compounds in the folic acid family have been synthesized, tested and discussed in the chemical and medical literature. The compounds have various activities at the enzymatic level; they inhibit such enzymes as dihydrofolate reductase, folyl polyglutamate synthetase, glycinamide ribonucleotide formyltransferase and thymidylate synthase.

More recently, a series of 4-hydroxypyrrolo[2,3-d]pyrimidin-L-glutamic acid derivatives have been disclosed and shown to be particularly useful antifolate drugs. See, for example, U.S. Pat. Nos. 4,966,206; 5,028,608; 5,106,974; and 4,997,838. However the synthetic route for the preparation of these compounds has not yet been optimized.

The present invention provides improved processes for the preparation of 4-hydroxy-5-substituted-ethynylpyrrolo[2,3-d]pyrimidine intermediates and 4-hydroxypyrrolo[2,3-d]pyrimidine-L-glutamic acid derivatives which are useful as antifolate drugs.

SUMMARY OF THE INVENTION

The present invention provides a one-pot process for preparing a compound of formula I

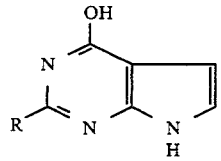

wherein
R is H, $C_1$-$C_4$ alkyl, or a substituent of the formula $R^1$-NH-;
$R^1$ is an amino protecting group;
Y is a silyl group or p-$C_6H_4COR^2$;
$R^2$ is OH, $OR^4$, or NHC*H (COOR$^3$) CH$_2$CH$_2$COOR$^3$;
$R^4$ is a carboxy protecting group;
the configuration about the carbon atom designated * is L; and
each $R^3$ is the same or different carboxy protecting group, which comprises a) reacting a silylating agent with a 4-hydroxypyrrolo[2,3-d]pyrimidine of formula II

wherein R is as defined above, in the presence of an inert organic solvent or mixture of inert organic solvents;

b) iodinating the reaction product from step a); and c) catalytically coupling the reaction product from step b) with a compound of formula III $$H-C\equiv C-Y \qquad III$$

wherein Y is as defined above.

Also provided by the present invention is a process for preparing a compound of formula IV

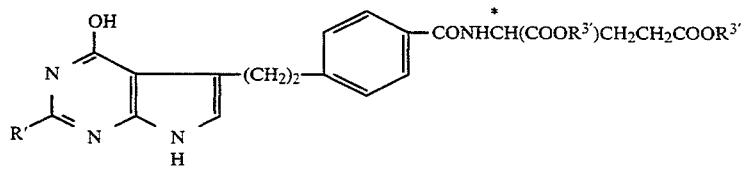

wherein
R' is H, $C_1$-$C_4$ alkyl, amino, or a substituent of the formula $R^1$-NH-;
$R^1$ is as defined above;
the configuration about the carbon atom designated * is L; and
each $R^{3'}$ is H or the same or different carboxy protecting group; or a salt thereof;

which comprises above steps a), b) and c), in which Y of a formula I compound is p-$C_6H_4COR^2$, $R^2$ is NHC*H(COOR$^3$)CH$_2$CH$_2$COOR$^3$, and * and $R^3$ are as defined above, which further comprises (d) reducing the ethynyl bridge of the reaction product of step c);

e) optionally deprotecting the reaction product from step d); and f) optionally salifying the reaction product from step e).

The present invention further provides a process for preparing a compound of formula IV

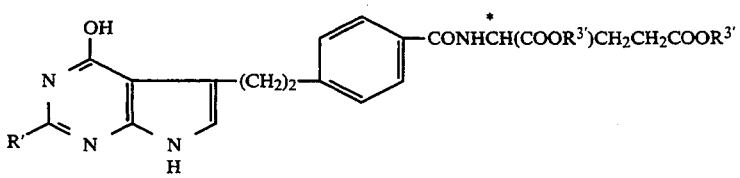

wherein
R' is H, $C_1$–$C_4$ alkyl, amino, or a substituent of the formula $R^1$-NH-;
$R^1$ and * are as defined above; and
each $R^{3'}$ is H or the same or different carboxy protecting group; or a salt thereof;
which comprises above steps a), b), and c), in which Y of a formula I compound is a silyl group, which further comprises
g) removing the Y silyl group;
h) coupling the reaction product from step g) with a compound of formula V

wherein * and $R^{3'}$ are as defined above, and X is bromo or iodo;
i) reducing the ethynyl bridge of the reaction product of step h);
j) optionally deprotecting the reaction product from step i); and
k) optionally salifying the reaction product from step j).

The present invention also provides a process for preparing a compound of formula IV

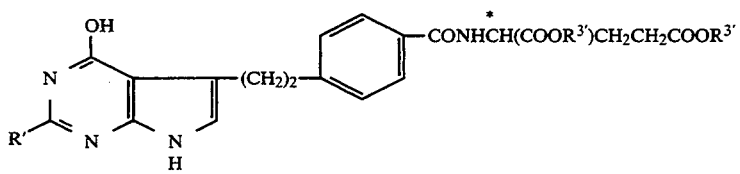

wherein
R' is H, $C_1$–$C_4$ alkyl, amino, or a substituent of the formula $R^1$—NH—;
$R^1$ is an amino protecting group;
the configuration about the carbon atom designated * is L; and
each $R^{3'}$ is H or the same or different carboxy protecting group;
or a salt thereof, which comprises above steps a), b), and c), in which Y of a formula I compound is p-$C_6H_4COR^2$, $R^2$ is OH or $OR^4$, and $R^4$ is a carboxy protecting group, which further comprises
l) coupling the reaction product from step c) with a compound of formula Va

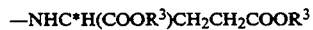

wherein $R^3$ and * are as defined above;
m) reducing the ethynyl bridge of the reaction product of step l);

n) optionally deprotecting the reaction product from step m); and
o) optionally salifying the reaction product from step n).

DETAILED DESCRIPTION OF THE INVENTION

One aspect of the present invention pertains to a one-pot process for the preparation of 4-hydroxy-5-substituted-ethynylpyrrolo[2,3-d]pyrimidines which are useful, inter alia, as intermediates in the preparation of complex antimetabolites of the antifolate type.

One of ordinary skill in the art will recognize that compounds of the present invention which contain a 4-hydroxypyrrolo[2,3-d]pyrimidine moiety exist in tautomeric equilibrium with the corresponding 4(3H)-oxo compounds. For illustrative purposes, the equilibrium of the tautomeric forms of this pyrrolo[2,3-d]pyrimidine moiety is shown below.

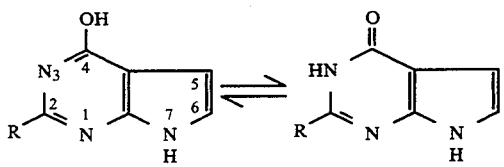

Throughout this specification, the 4-hydroxy tautomer is depicted and the corresponding nomenclature is used. However, it is understood that such depictions include the corresponding tautomeric 4(3H)-oxo forms.

The following definitions refer to various terms used above and throughout this disclosure.

The term "$C_1$–$C_4$ alkyl" refers to the straight or branched aliphatic chains of 1–4 carbon atoms including methyl, ethyl, propyl, isopropyl, n-butyl, isobutyl, sec-butyl and tertbutyl.

The amino protecting group designated $R^1$ in formulae throughout this specification (when R is a substituent of the formula $R^1$—NH—) denotes a group which generally is not found in a final therapeutic compound, but which is intentionally introduced during a portion of the synthetic process to protect an amino group which may otherwise react in the course of chemical manipulations, and is then removed at a later stage of the synthesis. Numerous reactions for the formation and removal of such a protecting group are described in a number of standard works including, for example, "Protective Groups in Organic Chemistry", Plenum Press, (London and New York, 1973); Greene, Th. W., "*Protecting Groups in Organic Synthesis*", Wiley, (New York, 1981); and "*The Peptides*", Vol. I, Schroöder and Lubke, Academic Press, (London and New York, 1965). Typically, an amide utilizing an acyl group which is selectively removable under mild conditions, such as for example, a formyl group, a lower alkanoyl group of from 2 to 8 carbon atoms which is substituted at the 1-position, such as trifluoroacetyl, are useful. A tertiary alkanoyl such as 2,2-dimethylpropionyl is especially useful. Other amino protecting groups include N-alkoxycarbonyls such as N-methoxycarbonyl, N-ethoxycarbonyl, N-(t-butyloxycarbonyl) and N-diisopropyl-methoxycarbonyl.

The term "lower alkanoyl group of from 1 to 8 carbon atoms" refers to straight or branched univalent aliphatic acyl groups of 1-8 carbon atoms including, for example, formyl, acetyl, propionyl, butyryl, α-methylpropionyl, valeryl, α-methylbutyryl, β-methylbutyryl, pivaloyl, octanoyl, and the like.

The term "carboxy protecting group" as used herein refers to one of the ester derivatives of the carboxylic acid group commonly employed to block or protect the carboxylic acid group while reactions are carried out on other functional groups on the compound. Examples of such carboxylic acid protecting groups include 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2', 4,4'-tetramethoxybenzhydryl, methyl, ethyl, propyl, isopropyl, t-butyl, t-amyl, trityl, 4-methoxytrityl, 4,4'-dimethoxytrityl, 4,4'4''-trimethoxytrityl, 2-phenylprop-2-yl, trimethylsilyl, t-butyldimethylsilyl, phenacyl, 2,2,2-tricholorethyl, β-(trimethylsilyl)ethyl, β-(di(n-butyl)methylsilyl-)ethyl, p-toluenesulfonylethyl, 4-nitrobenzylsulfonylethyl, allyl, cinnamyl, 1-(trimethylsilylmethyl)-prop-1-en-3-yl, and like moieties. The species of carboxy protecting group employed is not critical so long as the derivatized carboxylic acid is stable to the conditions of subsequent reaction(s) on other positions of the molecule and can be removed at the appropriate point without disrupting the remainder of the molecule. Further examples of these groups are found in E. Haslam, "*Protective Groups in Organic Chemistry*", J. G. W. McOmie, Ed., Plenum Press, New York, N.Y., 1973, Chapter 5, and T. W. Greene, "*Protective Groups in Organic Synthesis*", John Wiley and Sons, New York, N.Y., 1981, Chapter 5. A related term is "protected carboxy", which refers to a carboxy group substituted with one of the above carboxy protecting groups. Preferred protecting groups are methyl and ethyl.

As mentioned above, the process of the present invention includes the salt forms of compounds of formula IV. A compound of formula IV can possess a sufficiently acidic group, a sufficiently basic group, or both functional groups, and accordingly react with any of a number of inorganic bases, and inorganic and organic acids, to form a salt. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogen-phosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, and potassium carbonate. The potassium and sodium salt forms are particularly preferred.

When the intermediates of this invention are converted to final, pharmaceutically active compounds (compounds of formula IV in which $R^1$ is H and each $R^3$ is H), the salt form of those compounds must be of the pharmaceutically acceptable nature.

Processes for preparing acid addition, base addition, and pharmaceutically acceptable salts (salification) are well known in the art.

For preparing compounds of formula I, the starting material is a compound of formula II

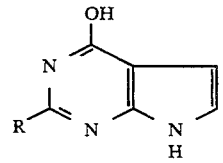

II wherein

R is H, $C_1$-$C_4$ alkyl, or a substituent of the formula $R^1$—NH—; and $R^1$ is an amino protecting group.

Formula II compounds are prepared by methods commonly known to organic chemists. For example, Davoll, J., *J. Chem, Soc.*, 131 (1960) describes the synthesis of 4-hydroxypyrrolo[2,3-d]pyrimidine. In addition, the synthesis of 2-methyl-, 2-ethyl-, 2-n-propyl- and 2-phenyl-4-hydroxypyrrolo [2,3-d]pyrimidines is described by West, R. A., et al., *J. Org. Chem.*, 26:3809–3812 (1961).

Preferred formula II compounds include unsubstituted 4-hydroxypyrrolo[2,3-d]pyrimidine and 2-methyl-4-hydroxypyrrolo[2,3-d]pyrimidine.

Other preferred formula II compounds include 2-amino-and 2-protected amino-4-hydroxypyrrolo[2,3-d]pyrimidines. The preferred method for the preparation of 2-amino-4-hydroxypyrrolo[2,3-d]pyrimidines and a representative method for protecting the 2-amino-substituent is taught in U.S. Pat. No. 5,235,053, which is herein incorporated by reference. Although amino protecting groups generally known in the art would adequately protect the 2-amino- substituent of formula II, an unsubstituted or substituted lower alkanoyl group of 1–8 carbon atoms is preferred. Of these, 2,2-dimethylpropionyl is especially preferred.

This first aspect of the present invention, a process for preparing a compound of formula I above, is carried out by
a) reacting a silylating agent with a 4-hydroxypyrrolo[2,3-d]pyrimidine of formula II in the presence of an inert solvent;
b) iodinating the reaction product from step a); and
c) catalytically coupling the reaction product from step b) with a compound of formula III

 III wherein Y is as defined above.

This process is carried out in situ, as a single process, in which each step is conducted immediately following the completion of the previous step.

In step a), generally known silylating agents are employed. See, for example, Calvin, E. W., "Silicon Reagents in Organic Synthesis", Academic Press, (London, et al., 1988). Particularly useful silylating agents include "tri-lower alkyl silyl" agents, the term of which contemplates triisopropylsilyl, trimethylsilyl and triethylsilyl, trimethylsilyl halides, silylated ureas such as bis(-trimethylsilyl)urea (BSU), and silylated amides such as N,O-bis(trimethylsilyl)acetamide (BSA). Of these, BSA is preferred.

In general, the addition of at least 1 molar equivalent of silylating agent to a formula II compound, in the presence of an inert organic solvent, is sufficient to drive the step a) reaction. However, it is advisable to use at least 2 molar equivalents of silylating agent per mole of substrate to optimize the silylation of formula II compounds. Suitable solvents for this reaction include, for example, tetrahydrofuran (THF) and, especially, dimethylformamide (DMF). It is preferable to run step a) of this process at a temperature in a range from about 25° to about 60° C. However, the optimum operating temperature for a given reaction is easily found according to the routine skill of organic chemists.

When bis(trimethylsilyl)acetamide is employed as the silylating agent, the reaction product is presumably a pyrrolo[2,3-d]pyrimidine of the formula

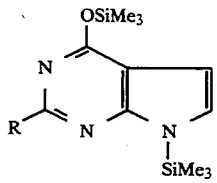 III wherein R is as defined above.

Ideally, step b), iodinating or brominating the reaction product from step a), is carried out immediately following the completion of step a), after the mixture is allowed to cool to ambient temperature.

Bromination and iodination of a reaction product from step a) is accomplished through methods known by one of ordinary skill in the art. For example, the addition of N-chlorosuccinimide to the mixture of a formula II compound, a silylating agent and an inert organic solvent, results in the conversion of the formula II compound to a C-5 chlorinated compound of formula II.

Similarly, bromination of a formula II compound at the C-5 position is accomplished via the addition of known brominating agents such as elemental bromine, N-bromoacetamide and N-bromosuccinimide. Of these, the use of N-bromosuccinimide is preferred.

Likewise, iodination of a formula II compound at the C-5 position is accomplished by the addition of known iodinating agents such as elemental iodine, iodine monochloride and N-iodosuccinimide. Of these, N-iodosuccinimide is preferred.

Depending upon the desired result, the selected halogenating agent should be added to the mixture in the amount of at least one molar equivalent per mole of substrate.

Step b) of the process is preferably run in the absence of light.

Step c) of the process, the catalytic coupling of a reaction product of step b) with a compound of formula III

 III wherein
Y is a silyl group or $p\text{-}C_6H_4COR^2$;
$R^2$ is OH, $OR^4$, or $-\text{NHC*H}(COOR^3)CH_2CH_2COOR^3$;
$R^4$ is a carboxy protecting group;
the configuration about the carbon atom designated * is L; and
each $R^3$ is the same or different carboxy protecting group, is accomplished via the methods taught by Taylor, et al., in U.S. Pat. No. 4,818,819 ('819), which is herein incorporated by reference.

Generally, the coupling reaction between a compound of formula III (which are disclosed by Taylor in the aforementioned '819 patent) and the reaction product from step b) is catalyzed by a palladium catalyst such as, for example, $Pd(Ph_3)_4$ and $PdCl_2$, in the presence of a copper(I) salt such as cuprous iodide. The reagents used in this reaction are those which previously have been employed and described by, for example, Metpoler, et al., *J. Org. Chem.*, 41(2):265 (1976); Chalk, et al., *J. Org. Chem.*, 41(7);1206 (1976); Arai, et al. *J. Heterocyclic Chem.*, 15:351 (1978); and Tamuru, et al., *Tetrahedron Letters*, 10:919 (1978).

More specifically, when Y of a formula III compound is a silyl group (preferably a trisubstituted silyl group such as trimethylsilyl), preferred catalysts include palladium(II) chloride and cuprous iodide in the presence of a trisubstituted phosphine such as triphenylphosphine.

When Y is $p\text{-}C_6H_4COR^2$, preferred catalysts include tetrakis(triphenylphosphine)palladium(0) and cuprous iodide.

These reactions preferably are conducted in the presence of at least one molar equivalent of a secondary or tertiary amine such as, for example, diethylamine or, especially, triethylamine, which acts as an acid acceptor. The reaction optionally is run under an inert atmosphere, preferably in the presence of an inert polar solvent or mixture of solvents such as, for example, acetonitrile, dimethylformamide (DMF), 1-methyl-2-pyrrolidinone, and the like. Of these, DMF is preferred. Typically, these reactions are run at ambient temperature.

The necessary reaction time for steps a), b), and c) is a function of the starting materials and the operating temperature. The optimum reaction time for a given process is, as always, a compromise which is found by considering the competing goals of throughput, which is favored by short reaction times, and maximum yield, which is favored by long reaction times.

Upon completion of this coupling step, the product is isolated, generally by mixing the reaction product of step c) with water, alcohol, or mixtures thereof. Desilylation of the 4- and 7-position silyl groups is spontaneous under these isolation procedures.

A further aspect of the present invention provides a process, when Y of a formula I compound is p-$C_6H_4COR^2$, $R^2$ is —$NHC^*H(COOR^3)CH_2CH_2COOR^3$ each $R^3$ is the same or different carboxy protecting group, and the configuration about the carbon atom designated * is L, for preparing a compound of formula IV

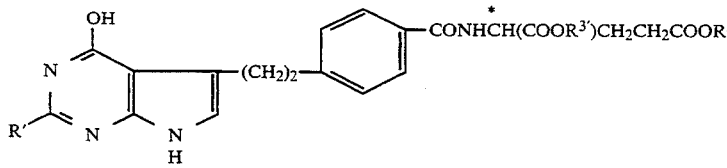

wherein

R' is H, $C_1$-$C_4$ alkyl, amino, or a substituent of the formula $R^1$—NH—;

$R^1$ and * are as defined above; and each $R^{3'}$ is H or the same or different carboxy protecting group; or a salt thereof, which comprises above steps a), b) and c), in which Y of the formula I compound is p-$C_6H_4COR^2$, $R^2$ is —$NHC^*H$-$(COOR^3)CH_2CH_2COOR^3$, and $R^3$ and * are as defined above, which further comprises (d) reducing the ethynyl bridge of the reaction product of step c);

e) optionally deprotecting the reaction product from step d); and f) optionally salifying the reaction product from step e).

Each of steps d), e and f), which are carried out after the reaction product of step c) is is isolated, also are known in the art and are carried out utilizing the procedures taught in U.S. Pat. No. 4,996,206, which is herein incorporated by reference.

Another aspect of the present invention provides a process, when Y of the formula I compound is a silyl group, for preparing a compound of formula IV

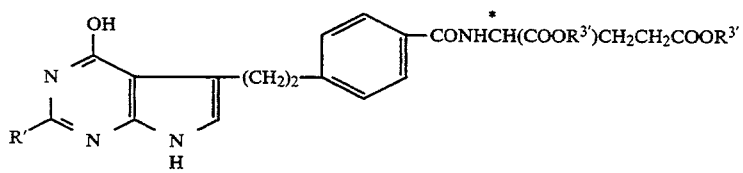

wherein

R' is H, $C_1$-$C_4$ alkyl, amino, or a substituent of the formula $R^1$—NH—;

$R^1$ and * are as defined above; and each $R^{3'}$ is H or the same or different carboxy protecting group; or a salt thereof; which comprises above steps a), b), and c), in which Y of the formula I compound is a silyl group, which further comprises g) removing the Y silyl group;

h) coupling the reaction product from step g) with a compound of formula V

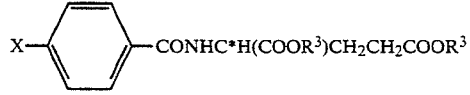

wherein $R^3$ and * are as defined above, and X is bromo or iodo;

i) reducing the ethynyl bridge of the reaction product of step h);

j) optionally deprotecting the reaction product from step i); and k) optionally salifying the reaction product from step j).

Procedures for carrying out process steps g), h), i), j), and k) are well known to one of ordinary skill in the organic arts.

Step g), which is carried out after the reaction product of step c) is isolated, involves the removal of the Y-substituent silyl group through known procedures (see, e.g., Colvin, E. W., supra).

Steps h), i), j) and k) are carried out utilizing the procedures taught in U.S. Pat. No. 4,996,206.

An additional aspect of the present invention provides a process for preparing a compound of formula IV

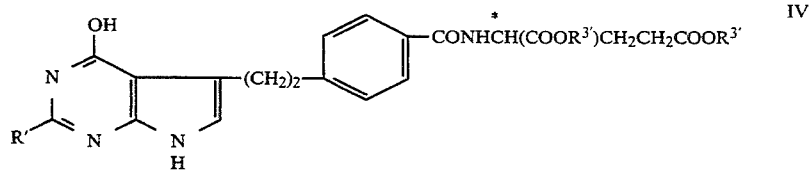

wherein

R' is H, $C_1$-$C_4$ alkyl, amino, or a substituent of the formula $R^1$—NH—;

$R^1$ is an amino protecting group;

the configuration about the carbon atom designated * is L; and each $R^{3'}$ is H or the same or different carboxy protecting group; or a salt thereof, which comprises above steps a), b), and c), in which Y of the formula I compound is p-$C_6H_4COR^2$, $R^2$ is OH or $OR^4$, and $R^4$ is a carboxy protecting group, which further comprises l) coupling the reaction product from step c) with a compound of formula Va

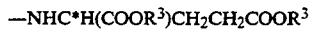　　　　　　Va wherein $R^3$ and * are as defined above;

m) reducing the ethynyl bridge of the reaction product of step l);

n) optionally deprotecting the reaction product from step m); and o) optionally salifying the reaction product from step n).

Steps l), m), n), and o), as well as compounds of formula Va, are taught in U.S. Pat. No. 5,248,775, which is herein incorporated by reference.

Compounds of formula IV in which $R^{3'}$ is H are known, pharmaceutically active compounds which are useful for treating susceptible neoplasms.

The following examples further illustrate the processes according to the present invention. The examples are not intended to be limiting to the scope of the invention, in any respect, and should not be so construed.

NMR spectra were obtained on a conventional 300 MHz spectrometer in deuterated dimethyl sulfoxide, and peak positions are reported as p.p.m. downfield from tetramethylsilane. NMR splitting patterns are designated by the following abbreviations: s, singlet; d, doublet; t, triplet; q, quartet; m, multipier; br, broad. Except as otherwise noted, HPLC analyses were carried out under the following conditions: 30 cm C18 column; mobile phase: A, acetonitrile; B, 1% aqueous acetic acid; gradient: 40% A-60% B to 60% A-40% B (linear) in 15 min; flow rate: 2.0 mL/min; detection at 254 nm. The following abbreviations for solvents and reagents are used: DMF -dimethylformamide; BSA- N,O-bis(trimethylsilyl)acetamide.

EXAMPLE 1

2-Amino-4-hydroxy-7H-pyrrolo[2,3-d]pyrimidine

A mixture of 136.7 g of bromoacetaldehyde diethylacetal, 347 mL of water, and 17.3 mL of concentrated HCl was heated to about 90° C. with vigorous stirring for about 30 minutes, at which time a clear solution was obtained. The solution was cooled to ambient temperature and 68.3 g of sodium acetate was added. The resulting solution was added, with stirring, to a suspension of 100 g of 2,4-diamino-6-hydroxypyrimidine and 34.2 g of sodium acetate in 739 mL of water, which had been heated to 70°-85° C. The reaction was allowed to proceed for 2 hours at 70°-85° C., at which time the reaction was complete. The mixture was cooled to 0° C. and stirred for about 1.5 hours. The mixture was then filtered and the collected product was washed with 500 mL of water and 500 mL of acetone, and dried, affording 72.3 g (79%) of 2-amino-4-hydroxy-7H-pyrrolo[2,3-d]pyrimidine, mp>300° C. NMR δ6.03 (s, 2H), 6.13 (m, 1H), 6.56 (dd, J=3.3, 2.3 Hz, 1H), 10.23 (br s, 1H), 10.93 (br s, 1H).

EXAMPLE 2

N-(4-Hydroxy-7H-pyrrolo[2,3-d]pyrimidin-2-yl)-2,2-dimethylpropionamide

A 50 g portion of the 2-amino-4-hydroxy-7H-pyrrolo[2,3-d]pyrimidine obtained from Example 1 was suspended in 225 mL of toluene, and the toluene was distilled until no further water separated. To the mixture was added 182.8 g of pivalic anhydride and 1.82 g of 4-dimethylaminopyridine. The temperature was increased to 140°-145° C., and residual toluene was removed by distillation. After about 8 hours, when the reaction was complete as indicated by HPLC analysis (30 cm C18 column; mobile phase: acetonitrile—1% aq. acetic acid 3:7; flow rate: 2.0 mL/min; detection at 254 nm) the reaction mixture was cooled to ambient temperature. t-Butyl methyl ether (TBME) was then added to precipitate the product, and the mixture was allowed to slowly cool to about −5° C. and filtered. The wet cake was reslurried with TBME, filtered, and dried. The product thus obtained was slurried with 1N HCl—DMF 9:1, filtered and dried, affording 45.7 g (65%), of N-(4-hydroxy-7H-pyrrolo[2,3d]pyrimidin-2-yl)-2,2-dimethylpropionamide, mp 296°-301° C. (dec). NMR δ1.19 (s, 9H), 6.36 (dd, J=.8, 3.2 Hz, 1H), 6.91 (dd, J=2.2, 3.2 Hz, 1H), 10.76 (br s, 1H), 11.54 (br s, 1H).

EXAMPLE 3

N-[4-[2-[2-(2,2-Dimethylpropionyl)amino-4-hydroxy-7H-pyrrolo[2,3-pyrimidin-5-yl]ethynyl]benzoyl]-L-glutamic acid diethyl ester To a solution of 1.0 g (4.27 mmol) of 2-(2,2-dimethylpropionyl)amino-4-hydroxypyrrolo[2,3-d]pyrimidine in 20 mL of dry DMF at 40° C. stirred under a nitrogen atmosphere was added with stirring 1.91 g (9.4 mmol) of N,O-bis(trimethylsilyl) acetamide (BSA) and the mixture stirred at 40° C. for 2 hours. After cooling to ambient temperature, there was added 1.15 g (5.12 mmol) of N-iodosuccinimide and the resulting mixture was stirred at ambient temperature for about 1.5 hours. The progress of the iodination reaction could be monitored by HPLC analysis. To the mixture was added 1.70 g (5.12 mmol) of N-(4-ethynyl)benzoyl-L-glutamic acid diethyl ester and the resulting mixture was degassed by alternate application of vacuum and nitrogen purging. Then was added 493 mg (0.423 mmol) of tetrakis(triphenylphosphine)palladium(0), 163 mg (0.854 mmol) of cuprous iodide, and 0.86 g (8.5 mmol) of triethylamine and the resulting mixture was stirred at ambient temperature overnight. The DMF was substantially removed by vacuum evaporation and the residue triturated with 40 mL of ethanol. The resulting suspension was filtered, washed with ethanol, and dried to give 1.78 g (74% overall) of N-[4-[2-[2- (2,2-dimethylpropionyl)amino-4-hydroxy -7H-pyrrolo[2,3-d]pyrimidin-5-yl]ethynyl]benzoyl]-L-glutamic acid diethyl ester as a tan colored solid, mp 264°-270° C. (dec), 93% pure by HPLC analysis. An analytical sample was prepared by flash chromatography of a portion of the material, mp 262°-267° C. NMR δ1.16 (t, J=7.2 Hz, 6H), 1.23 (s, 9H), 2.04 (m, 2H), 2.44 (t, J=7.5 Hz, 2H), 4.03 (q, J=7.1 Hz, 2H), 4.11 (q, J=7.1 Hz, 2H), 4.43 (m, 1H), 7.45 (s, 1H), 7.52 (d, J=8.3 Hz, 2H), 7.89 (d, J=8.3 Hz, 2H), 8.80 (d, J=7.4 Hz, 1H), 10.91 (br s, 1H), 11.91 (br s, 1H), 12.03 (br s, 1H); IR (KBr) 3226, 2978, 2120, 1739, 1658, 1618, 1539, 1246, 1171 cm$^{-1}$; UV (EtOH) 327 nm (ε20,800), 271 (ε17,000), 226 (ε12,400). Anal. Calcd for $C_{29}H_{33}N_5O_6$: C, 61.80; H, 5.90; N, 12.43. Found: C, 61.89; H, 5.90; N, 12.66.

EXAMPLE 4

N-[4-Hydroxy-5-(trimethylsilyl)ethynyl-7H-pyrrolo[2,3-d]pyrimidin-2-yl]-2,2-dimethylpropionamide To a solution of 20.0 g (85.4 mmol) of 2-(2,2-dimethylpropionyl)amino-4-hydroxypyrrolo[2,3-d]pyrimidine in 160 mL of dry DMF stirred in a dry atmosphere was added 38.2 g (187.8 mmol) of BSA and the mixture was heated to 40° C. for 3 hours. After cooling to about 0° C. in an ice bath there was added 23.1 g (102.5 mmol) of N-iodosuccinimide as a solid. The mixture was stirred at 0° C. for 15 minutes, then allowed to warm to ambient temperature overnight. To the resulting mixture, maintained under a nitrogen atmosphere, was added sequentially 12.6 g (128 mmol) of (trimethylsilyl) acetylene, 17.3 g (171 mmol) of triethylamine, 3.25 g ( 17.1 mmol) of cuprous iodide, and a preformed mixture prepared by adding 1.51 g (8.5 mmol) of palladium (II) chloride and 4.48 g (17.1 mmol) of triphenylphosphine to 40 mL of DMF. The resulting solution was stirred at ambient temperature for 2 hours. At this point, HPLC analysis of an aliquot indicated complete conversion of the in situ-derived N-(4-hydroxy-5-iodo-7H-pyrrolo[2,3-d]pyrimidin-2-yl)-2,2-dimethylpropionamide. The reaction mixture was poured into 500 mL of acetonitrile and 12 mL of water was added, causing the product to precipitate. After stirring for about 15 minutes, the product was filtered, washed with acetonitrile, and dried, affording 18.6 g (66%) of N-[4-hydroxy-5-(trimethylsilyl) ethynyl-7H-pyrrolo [2,3-d]pyrimidin-2-yl]-2,2-dimethyl propionamide as a light tan solid, mp>300° C. NMR δ0.18 (s, 9H), 1.22 (s, 9H), 7.33 (s, 1H), 10.9 (br s, 1H), 11.8 (br s, 1H), 11.9 (br s, 1H); IR (KBr) 3229, 2155, 1678, 1658, 1619, 1434, 1244, 1180, 1069 cm$^{-1}$; UV (EtOH) 285 nm (ε15,400), 250 nm (ε16,000). Anal. Calcd for $C_{16}H_{22}N_4O_2Si$: C, 58.15; H, 6.71; N, 16.95. Found: C, 57.58; H, 6.87; N,16.96.

EXAMPLE 5

N-(4-Hydroxy-5-ethynyl-7H-pyrrolo[2,3-d]pyrimidin-2-yl)-2,2-dimethylpropionamide To a mixture of 5.0 g (15.1 mmol) of N-[4-hydroxy-5-(trimethylsilyl) ethynyl-7H-pyrrolo[2,3-d]pyrimidin-2-yl]-2,2-dimethylpropionamide, in 40 mL of DMF and 10 mL of tetrahydrofuran was added 6.6 g (15.1 mmol) of tetrabutylammonium fluoride hydrate and the resulting solution was stirred at ambient temperature for 3.5 hours. After addition of 1.18 g of acetic acid and stirring for 15 minutes the mixture was poured into 50 mL of water. After stirring for about 1 hour the resulting suspension was filtered and the precipitate washed with water and dried, affording 3.38 g (86%) of N-(4-hydroxy-5-ethynyl-7H-pyrrolo[2,3-d]pyrimidin-2-yl)-2,2-dimethylpropionamide, mp>300° C. NMR δ1.21 (s, 9H) , 3.89 (s, 1H), 7.28 (s, 1H), 10.82 (br s, 1H), 11.82 (br s, 1H), 11.85 (br s, 1H); IR (KBr) 3354, 3250, 2973, 2120, 1699, 1676, 1608, 1536, 1433, 1243 cm$^{-1}$; UV (EtOH) 292 nm (ε13,900), 280 nm (ε14,500), 236 nm (ε14,900). Anal. Calcd for $C_{13}H_{14}N_4O_2$: C, 60.46; H, 5.46; N, 21.69. Found: C, 60.25; H, 5.32; N, 21.49.

EXAMPLE 6

N-[4-[2-[2-(2,2-Dimethylpropionyl)amino-4-hydroxy-7H-pyrrolo[2,3-d]pyrimidin-5-yl]ethynyl]benzoyl]-L-glutamic acid diethyl ester To a suspension of 3.33 g (12.9 mmol) of N-(4-hydroxy-5-ethynyl-7H-pyrrolo[2,3-d]pyrimidin-2-yl)-2,2-dimethylpropionamide in 64 mL of acetonitrile stirred under nitrogen was added 5.77 g (28.4 mmol) of BSA and the resulting mixture was stirred at 40° C. for 2 hours, then cooled to ambient temperature. To the resulting solution was added sequentially 5.58 g (12.9 mmol) of N-4-iodobenzoyl-L-glutamic acid diethyl ester, 2.6 g (25.8 mmol) of triethylamine, and a mixture of 0.114 g (0.65 mmol) of palladium(II) chloride and 0.338 g (1.29 mmol) of triphenylphosphine in 16 mL of acetonitrile. The resulting mixture was heated under reflux overnight (18 hours), after which time HPLC analysis of an aliquot indicated complete conversion of the (acetylenic) starting material. The mixture was cooled to ambient temperature and 2 mL of water was added. The resulting suspension was stirred for 30 minutes, filtered, and the precipitate washed with acetonitrile and dried, affording 6.15 g (85%) of N-[4-[2-[2-(2,2-dimethylpropionyl)amino-4-hydroxy-7H-pyrrolo[2,3-d]pyrimidin-5-yl ]ethynyl]benzoyl]-L-glutamic acid diethyl ester as a tan solid. The melting point and NMR spectral data for the product were in agreement with data obtained on an authentic sample prepared by the procedure of Example 3.

We claim:

1. A process for preparing a compound of formula I

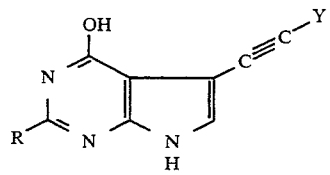

wherein

R is H, $C_1$-$C_4$ alkyl, or a substituent of the formula $R^1$—NH—;

$R^1$ is an amino protecting group;

Y is ($C_1$-$C_4$ alkyl)$_3$Si— or p-$C_6H_4COR^2$;

$R^2$ is OH, $OR^4$, or NHC*H (COOR$^3$)CH$_2$CH$_2$COOR$^3$;

$R^4$ is a carboxy protecting group;

the configuration about the carbon atom designated * is L; and each $R^3$ is the same or different carboxy protecting group, which comprises a) reacting a silylating agent with a 4-hydroxypyrrolo[2,3-d]pyrimidine of formula II

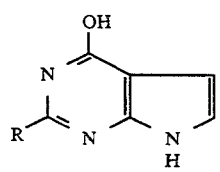

wherein R is as defined above, in the presence of an inert organic solvent or mixture of inert organic solvents;

b) iodinating the reaction product from step a);
c) catalytically coupling the reaction product from step b) with a compound of formula III

H—C≡C—Y    III wherein Y is as defined above; and
d) treating the reaction products with water or an alcohol.

2. The process of claim 1 wherein said silylating agent is bis(trimethylsilyl)acetamide.

3. The process of claim 2 wherein said inert organic solvent is N,N-dimethylformamide.

4. The process of claim 3 wherein said iodinating ms accomplished using N-iodosuccinimide.

5. The process of claim 4 wherein said catalyst is a palladium catalyst in the presence of a Cu(I) salt.

6. The process of claim 5 wherein R is a substituent of the formula $R^1$—NH—.

7. The process of claim 6 wherein $R^1$ is pivaloyl.

8. The process of claim 7 wherein Y is (a silyl group) $(C_1-C_4\ alkyl)_3Si$—.

9. The process of claim 8 wherein said silyl group is $Si(CH_3)_3$.

10. The process of claim 7 wherein Y is p-$C_6H_4COR^2$.

11. The process of claim 10 wherein $R^2$ is OH or $OR^4$.

12. The process of claim 10 wherein $R^2$ is $HNC^*H(COOR^3)CH_2CH_2COOR^3$.

13. The process of claim 12 wherein each $R^3$ is the same carboxy protecting group.

14. The process of claim 13 wherein each $R^3$ is ethyl.

15. The process of claim 1 wherein R is a substituent of the formula $R^1$—NH—, $R^1$ is an amino protecting group, Y is p-$C_6H_4COR^2$, $R^2$ is $NHC^*H(COOR^3)CH_2CH_2COOR^3$, and each $R^3$ is the same or different carboxy protecting group.

16. A process according to claim 1 for preparing a compound of formula IV

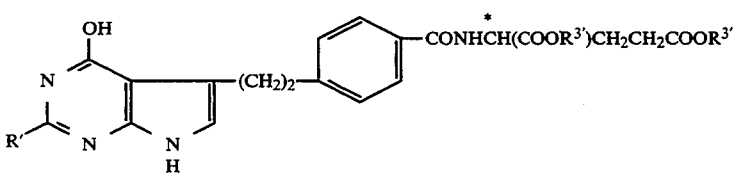

wherein
R' is H, $C_1-C_4$ alkyl, amino, or a substituent of the formula $R^1$—NH—;
$R^1$ is an amino protecting group;
the configuration about the carbon atom designated * is L; and
each $R^{3'}$ is H or the same or different carboxy protecting group;
or a salt thereof, in which Y of a formula I compound is p-$C_6H_4COR^2$, and $R^2$ is $NHC^*H(COOR^3)CH_2CH_2COOR^3$, which further comprises e) reducing the ethynyl bridge of the reaction product of step d);
f) optionally deprotecting the reaction product from step e); and
g) optionally salifying the reaction product from step f).

17. The process of claim 16 wherein R' is a substituent of the formula $R^1$—NH—, $R^1$ is pivaloyl, and each $R^{3'}$ is the same carboxy protecting group.

18. The process of claim 17 wherein each $R^{3'}$ is ethyl.

19. The process of claim 16 wherein R' is amino and each $R^{3'}$ is H.

20. A process according to claim 1 for preparing a compound of formula IV

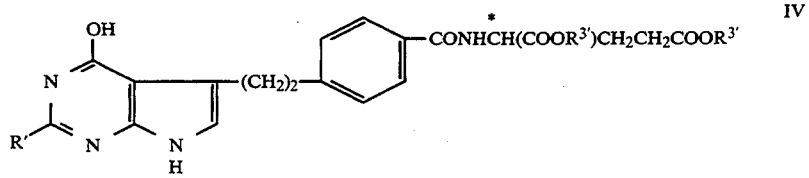

wherein
R' is H, $C_1-C_4$ alkyl, amino, or a substituent of the formula $R^1$—NH—;
$R^1$ is an amino protecting group;
the configuration about the carbon atom designated * is L; and
each $R^{3'}$ is H or the same or different carboxy protecting group; or a salt thereof, in which Y of a formula I compound is a silyl group, which further comprises h) removing the Y silyl group;
i) coupling the reaction product from step h) with a compound of formula V

wherein * and $R^3$ are as defined above, and X is bromo or iodo;
i) reducing the ethynyl bridge of the reaction product of step i);
k) optionally deprotecting the reaction product from step j); and
l) optionally salifying the reaction product from step k).

21. The process of claim 20 wherein R' is a substituent of the formula $R^1$—NH—, $R^1$ is pivaloyl, and each $R^{3'}$ is the same carboxy protecting group.

22. The process of claim 21 wherein each $R^{3'}$ is ethyl.

23. The process of claim 20 wherein R' is amino and each $R^{3'}$ is H.

24. A process according to claim 1 for preparing a compound of formula IV

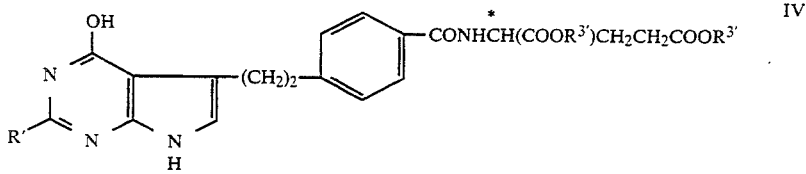

IV wherein
- R' is H, $C_1$–$C_4$ alkyl, amino, or a substituent of the formula $R^1$—NH—;
- $R^1$ is an amino protecting group;
- the configuration about the carbon atom designated * is L; and
- each $R^{3'}$ is H or the same or different carboxy protecting group; or a salt thereof, in which Y of a formula I compound is p-$C_6H_4COR^2$, $R^2$ is OH or $OR^4$, and $R^4$ is a carboxy protecting group, which further comprises m) coupling the reaction product from step d) with a compound of formula Va

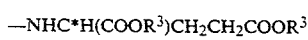    Va wherein $R^3$ and * are as defined above;

n) reducing the ethynyl bridge of the reaction product of step m);

o) optionally deprotecting the reaction product from step n); and p) optionally salifying the reaction product from step o).

25. The process of claim 24 wherein $R^1$ is a substituent of the formula $R^1$—NH—, $R^1$ is pivaloyl, and each $R^{3'}$ is the same carboxy protecting group.

26. The process of claim 25 wherein each $R^{3'}$ is ethyl.

27. The process of claim 24 wherein $R^1$ is amino and each $R^{3'}$ is H.

* * * * *